Jan. 2, 1968 T. O. MAHAFFEY Plant Pat. 2,784
AGLAONEMA PLANT
Filed Oct. 13, 1966
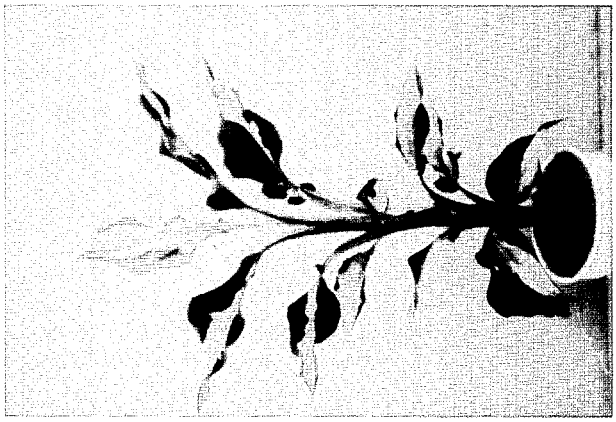
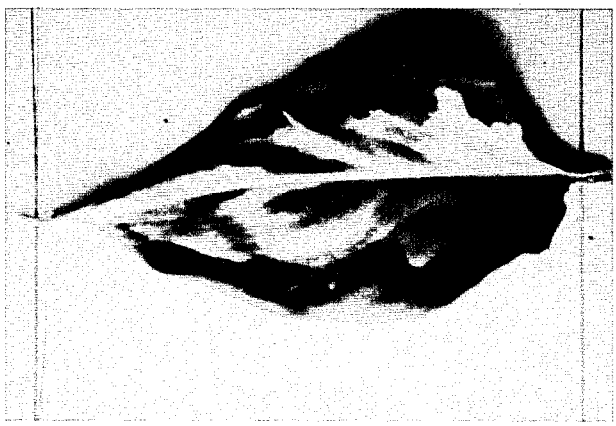
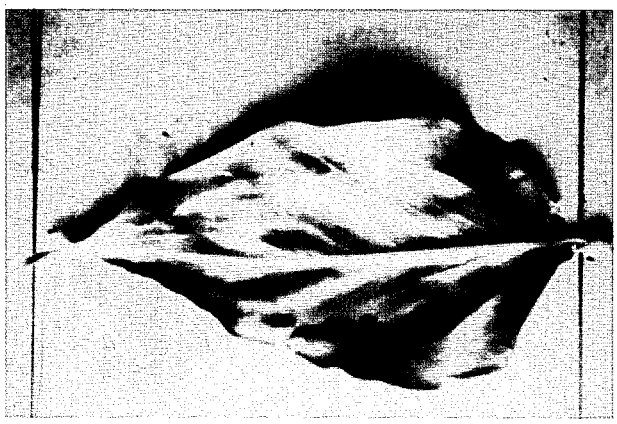
Inventor.
T. O. Mahaffey
By: Robb & Robb
Attorneys.

United States Patent Office

Plant Pat. 2,784
Patented Jan. 2, 1968

2,784
AGLAONEMA PLANT

Thomas O. Mahaffey, Apopka, Fla., assignor to Francis L. Stutzman, Maitland, and Robert W. Stutzman, Orlando, Fla.

Filed Oct. 13, 1966, Ser. No. 586,579
1 Claim. (Cl. Plt.—88)

The present invention relates to a new and distinct variety of Aglaonema plant, which was discovered by me on my cultivated property adjacent to Lake Marshall, near Apopka, Fla., as a sport of the Aglaonema variety known as "Simplex" (unpatented).

At the time of my discovery aforesaid, I was growing a bed of Aglaonema "Simplex" plants in a shade house, and my attention was attracted to one particular plant in this bed which bore some variegated leaves quite different from the other leaves on this plant and from all the other plants in this bed. Upon close inspection of this particular plant, I found that it had sported from a stem several inches from the ground, and I accordingly took immediate steps to preserve the sport and keep it under close observation, as well as to propagate the same from cuttings taken from the sport, as performed by me on my property aforesaid, as well as on property of my joint assignees, also located at Apopka, Fla. Continued observations and tests of the sport and the progeny thereof have convinced me that it represents a new and distinct variety which is distinctly different from the parent variety, as well as from all other Aglaonema varieties of which I am aware, as evidenced by the following unique combination of characteristics which are outstanding therein:

(1) Closer internodes than in the parent variety, Aglaonema "Simplex," with consequent production of many more leaves;

(2) Shorter petioles;

(3) Smaller, ruffled leaves; and (4) An attractive and sharply distinct variegation of the leaf color, with a Yellowish Chartreuse Green center, abruptly changing to Dark Green around the outer edge of the leaf and creating the impression of a hand-painted effect without any blending of the colors.

The accompanying drawing shows a typical specimen plant of my new variety, as well as the upper and under surfaces of a typical specimen leaf on an enlarged scale, all as depicted in color as nearly true as it is reasonably possible to make the same in a color illustration of this character.

The following is a detailed description of my new Aglaonema variety, as based on observations of specimen plants grown at Apopka, Fla., with color terminology in accordance with Maerz and Paul Dictionary of Color, except where general color terms of ordinary dictionary significance are obvious:

Parentage: Sport of Aglaonema "Simplex."

Propagations: Holds its distinguishing characteristics through succeeding propagations by cuttings (both tip cuttings and eye cuttings).

*Plant*

Form: Much-branched; upright; compact.

Growth: Vigorous.

Blooming habit: Although parent variety blooms in late spring to early summer, the new variety has never bloomed and probably never will under normal cultural conditions in Florida.

Foliage:

*Size.*—Medium.

*Quantity.*—Abundant.

*Color.*—New foliage: upper side—Cosack Green, Plate 23–11J around outer edge, abruptly changing to Piquant Green, Plate 20–6K in center of leaf; under side—Brunswick Green LTP, Plate 22–10L, around outer edge, changing to Apple Green, Plate 19–6J in center of leaf. Old foliage: upper side—Deep Chrome Green, Plate 24–12H around outer edge, abruptly changing to Parrot Green, Plate 21–6L in center of leaf, becoming Reed Green, Plate 19–12D under higher light intensity; under side—Mt. Vernon Green, Plate 23–8J around outer edge, changing to Verabsinthe Green, Plate 20–5J in center of leaf.

*Shape.*—Oval pointed; lanceolate.

*Texture.*—Upper side—leathery; glossy; corrugated. Under side—rough.

*Margin.*—Irregular; ruffled.

*Disease resistance.*—Very resistant to ordinary diseases to which Aglaonema plants are subject, as determined by comparison with parent variety grown under the same cultural conditions at Apopka, Fla.

*Flowers*

Flower: None produced.

*General observations*

Hardiness: Very good; withstands temperatures ranging from 32° to 105° F., as grown and observed in Apopka, Fla.

I claim:

1. A new and distinct variety of Aglaonema plant, substantially as herein shown and described, characterized particularly as to novelty by the unique combination of having closer internodes than in the parent variety Aglaonema "Simplex" (unpatented), with consequent production of many more leaves, shorter petioles, smaller ruffled leaves, and an attractive and sharply distinct variegation of the leaf color, with a Yellowish Chartreuse Green center, abruptly changing to Dark Green around the outer edge of the leaf and creating the impression of a hand-painted color effect without any blending of the leaf colors.

No references cited.

ROBERT E. BAGWILL, *Primary Examiner.*